(12) United States Patent
Burnouf et al.

(10) Patent No.: US 9,034,646 B2
(45) Date of Patent: May 19, 2015

(54) VIRALLY-INACTIVATED GROWTH FACTORS-CONTAINING PLATELET LYSATE DEPLETED OF PDGF AND VEGF AND PREPARATION METHOD THEREOF

(71) Applicants: Thierry Burnouf, Lille (FR); Cheng-Yao Su, Taipei (TW)

(72) Inventors: Thierry Burnouf, Lille (FR); Cheng-Yao Su, Taipei (TW)

(73) Assignee: ZHENG YANG BIOMEDICAL TECHNOLOGY CO., LTD., Taipei (TW)

( * ) Notice: Subject to any disclaimer, the term of this patent is extended or adjusted under 35 U.S.C. 154(b) by 8 days.

(21) Appl. No.: 13/684,746

(22) Filed: Nov. 26, 2012

(65) Prior Publication Data

US 2013/0143810 A1    Jun. 6, 2013

Related U.S. Application Data

(63) Continuation of application No. PCT/IB2011/052278, filed on May 25, 2011.

(30) Foreign Application Priority Data

May 25, 2010    (EP) .................... 10163843

(51) Int. Cl.
| | | |
|---|---|---|
| C12N 5/08 | (2006.01) | |
| A61K 35/16 | (2006.01) | |
| C12N 5/00 | (2006.01) | |
| A61K 38/18 | (2006.01) | |
| A61K 38/30 | (2006.01) | |

(52) U.S. Cl.
CPC .......... *C12N 5/0018* (2013.01); *A61K 38/1808* (2013.01); *A61K 38/1841* (2013.01); *A61K 38/30* (2013.01); *A61K 35/19* (2013.01)

(58) Field of Classification Search
None
See application file for complete search history.

(56) References Cited

FOREIGN PATENT DOCUMENTS

| EP | 0685490 A1 | 12/1995 |
|---|---|---|
| EP | 1685852 A1 | 8/2006 |
| EP | 2077118 A1 | 7/2009 |
| EP | 2389942 A1 | 11/2011 |
| WO | 9515763 A1 | 6/1995 |
| WO | 2008034803 A1 | 3/2008 |
| WO | 2009087560 A1 | 7/2009 |
| WO | WO 2009/118331 | * 10/2009 |
| WO | 2010033605 A2 | 3/2010 |
| WO | 2011148326 A1 | 12/2011 |

OTHER PUBLICATIONS

Burnouf Pierre-Alain et al: "A novel virally inactivated human platelet lysate preparation richin TGF-beta, EGF and IGF, and depleted of PDGF and VEGF", Biotechnology and Applied Biochemistry, London: Portland Press, vol. 56, No. 4, Aug. 1, 2010, pp. 151-160, XP009150255, ISSN: 1470-8744.
El-Ekiaby M et al: "Solvent-detergent filtered (S/D-F) fresh frozen plasma and cryoprecipitate minipools prepared in a newly designed integral disposable processing bag system", Transfusion Medicine (Oxford, England): Feb. 2010, LNKD-PUBMED: 19778318, vol. 20, No. 1, Feb. 2010, pp. 48-61, XP002650788, ISSN: 1365-3148.
Ferrara et al., The Biology of VEGF and Its Receptors, Nature Medicine, Jun. 2003, pp. 669-676, vol. 9, No. 6.
FDA Communication About an Ongoing Safety Review of Regranex (Becaplermin), http://www.fda.gov/Drugs/DrugSafety/PostmarketDrugSafetyInformationfor PatientsandProviders, Mar. 27, 2008, 1 page.
J.P.R. Pelletier et al., Pathogen Inactivation Techniques, Best Practice & Research Clinical Haematology, 2006, pp. 205-242, vol. 19, No. 1, Pub. Elsevier Ltd.
Stroncek et Rebulla, Platelet Transfusions, The Lancet, www.thelancet.com, Aug. 4, 2007, pp. 427-438, vol. 370.

* cited by examiner

*Primary Examiner* — Marianne P Allen
(74) *Attorney, Agent, or Firm* — Additon, Higgins & Pendleton, P.A.

(57) ABSTRACT

The invention concerns human platelet extracts rich in growth factors (PGF) for wound healing and stem cell expansion. Accordingly the subject invention relates to a virally-inactivated growth factors-containing platelet lysate depleted of PDGF and VEGF, which is preferably enriched in TGF, IGF and EGF-rich. The present invention further concerns a method for obtaining a platelet lysate comprising the steps of contacting a starting platelet concentrate with a solvent and/or a detergent, incubating the starting platelet concentrate with the solvent and/or detergent for a period of at least 5 minutes to 6 hours, at a pH maintained in a range from about 6.0 to about 9.0, and at a temperature within the range of from 2° C. to 50° C., optionally removing the solvent and/or the detergent by oil extraction and obtaining an aqueous protein phase, and incubating the solvent and/or detergent-treated platelet concentrate or the aqueous protein phase with charcoal.

13 Claims, 4 Drawing Sheets

VIRALLY-INACTIVATED GROWTH FACTORS-CONTAINING PLATELET LYSATE DEPLETED OF PDGF AND VEGF AND PREPARATION METHOD THEREOF

CROSS-REFERENCE TO PRIORITY APPLICATION(S)

This application is a continuation of the commonly assigned International Patent Application No. PCT/IB2011/052278 (filed May 25, 2011), and the commonly assigned European Patent Application No. 10 163843.5 (filed May 25, 2010, in the European Patent Office), both of which are hereby incorporated by reference in their entirety.

FIELD OF THE INVENTION

The present invention relates to the field of platelet derivatives and more specifically to the field of growth factors concentrates which are obtained from platelets from human or animal origin. The present invention also relates to methods for preparing such growth factors-containing platelet lysates, as well as to the use thereof for in vitro, ex vivo cell culture (such as for stem cell expansion and differentiation), cosmetic applications or clinical applications, for instance in combination with bone grafts.

BACKGROUND

As evidenced by proteomics analyses, human platelets contain a myriad of molecules exhibiting important physiological functions, among which growth factors (GF) are of particular interest. These growth factors, which accumulate within the platelet α-granules, mainly include three Platelet-Derived Growth Factors isoforms (PDGF-AA, -AB, and -BB), Vascular Endothelial Growth Factor (VEGF), Transforming Growth Factor-β (TGF-β1 and TGF-β2), Epidermal Growth Factor (EGF), Fibroblast Growth Factor (FGF), and some Insulin-like Growth Factor (IGF). According to the therapeutic interest of such growth factors, complex human platelet growth factors mixtures are already being used for therapeutic applications in the form of single-donor platelet gel biomaterials resulting from the activation of platelet-containing plasma by thrombin.

Platelet activation generally leads to the release of the growth factors contained therein and their entrapment into a gel matrix obtained by simultaneous thrombin-induced conversion of fibrinogen into fibrin. This biomaterial is generally applied on tissues, alone or in combination with graft materials. Growth factors-containing platelet gels are thus used in regenerative medicine to promote the healing and regeneration of soft and hard tissues. The growth factors concentrates obtained from platelets are also used for supplementing the growth media for in vitro or ex vivo cell cultures. Recently, the possibility to use human growth factors-rich platelet releasates as substitute for fetal bovine serum (FBS) for ex-vivo expansion of mesenchymal or hematopoietic stem cells has been demonstrated.

The use of growth factors-rich platelets releasates is of particular interest for expanding stem cells, and more specifically Mesenchymal stem cells (MCS) (or hematopoietic stem cells) which are considered as emergent "universal" cells, as a substitute for Fetal Bovine Serum (FBS) or Fetal Calf Serum (FCS) which are considered as possible sources of prion and virus transmission, as well as a cause for immunological problems in patients due to residual bovine proteins and antigens within the Bovine or Calf serum.

New approaches were recently developed, consisting in the production of recombinant platelet growth factors in conventional expression systems. For instance, some recombinant individual human (Rh) growth factors are used for therapeutic applications. Rh-PDGF-BB expressed by genetically-engineered yeast is in particular licensed in some countries for the treatment of chronic neuropathic lower-extremity diabetic ulcers although large doses and several weeks application of this single growth factor appear needed to achieve clinical efficacy. Similarly, Rh-bone morphogenetic proteins (BMP)-2 and -7, which belong to the TGF-β superfamily, can be produced from Chinese Hamster Ovary cells, and are licensed to heal some fracture surgery. However, the number of available recombinant growth factors remain extremely limited, which is in part due to the difficulty to isolate, identify, clone and express these growth factors. Furthermore, platelet-derived preparations still provide a supplementary benefit over the use of single recombinant factors, since a beneficial synergistic effect of growth factors combination can be achieved in some applications.

It nevertheless appears that the growth factors PDGF and VEGF were shown to be directly linked to the abnormal propagation and/or differentiation of cells (see for instance Ferrara et al., Nature Medicine, vol. 9, no. 6, 2003, pp. 669-676; as well as in the publication EMA/92326/2010 of the European Medical Agency dated Feb. 18, 2010, and in the communication of the FDA dated Mar. 27, 2008 about "an ongoing safety review of regranex (becaplermin). In view of the increased susceptibility of developing cancers upon treatment with each of these two growth factors, PDGF and VEGF are thus to be avoided for culturing stem cells or for healing patients, in particular when said patients are known to be at risk of cancer.

There is therefore a need for developing processing methods of human platelet materials allowing the preparation of well-characterized virally-safe industrial growth factors preparations, and more particularly of preparations depleted in PDGF and VEGF.

Patent Application WO 2009/087560 discloses that human platelet concentrates can be subjected to a treatment by a combination of solvent and detergent (S/D) that achieves dual purposes: (a) the inactivation of lipid-enveloped viruses and (b) the massive release of the growth factors from the platelet α-granules. A standardized complex platelet growth factors mixture comprising PDGF-AB, -BB, and -AA, TGF-β, EGF, VEGF, and insulin-like growth factor-β1 (IGF-β1), could then be obtained by combining S/D treatment, oil extraction and hydrophobic interaction chromatography (HIC), wherein oil extraction and HIC were used to remove the S/D agents without affecting significantly the PGF and protein content. The resulting platelet growth factors preparation was shown to stimulate various cell lines in vitro, and enhanced the expansion of stem cells from lipo-aspirated fat tissue. In addition, WO 2009/087560 discloses that replacing the HIC by a SP-sepharose cation-exchange column allows the preparation of a purified PDGF-VEGF fraction. In this approach, PDGF and VEGF are indeed adsorbed on the column but TGF-β, EGF, IGF are found in the breakthrough, together with the S/D agents used for the virus inactivation step. Conversely, WO 2009/087560 discloses that TGF-β and EGF may be purified to a certain extent by replacing the HIC by a DEAE-sepharose-anion-exchanger.

In the publication El-Ekiaby et al. (El-Ekiaby et al; "Solvent-detergent filtered (S/D-F) fresh frozen plasma and cryoprecipitate minipools prepared in a newly designed integral disposable processing bag system", Transfusion medicine, 2010, 20, 48-61), the authors disclose a process applied for the viral inactivation treatment of singulet or mini-pools of plasma and cryoprecipitate for transfusion and comprising, as major steps, the S/D treatment of Fresh Frozen Plasma (FFP) or of Cryo-Poor Plasma (CPP), or of cryoprecipitate with a mixture of TnBP and TRITON X-45®, the oil extraction of the S/D treated plasma material, and the filtering of the oil-extracted plasma material through an S/D adsorption filter containing activated charcoal. As discussed in this publication, the disclosed method in particular preserves the functional activity of plasma proteins (such as clotting factors), does not alter the VWF multimer composition, reduces TnBP and TRITON X-45® below acceptable levels, and allows the sterile filtration of the resulting purified plasma by gravity. This publication is nevertheless exclusively directed to plasma material purification and thus fails to disclose or even suggest a method which could be implemented for purifying growth factors from platelet concentrates.

The present inventors have now found surprisingly and after intensive research, that a process comprising a S/D treatment of a platelet concentrate, an oil extraction and a charcoal extraction, or a charcoal extraction only, permits the easy, rapid and efficient preparation of a virally inactivated growth factors containing platelet lysate which is depleted in both PDGF and VEGF, and wherein solvent and detergent concentrations are meeting the limits approved by regulatory authorities for S/D-treated parenteral blood-derived therapeutic products.

In particular, the method of the invention does not modify the content in the major proteins, such as albumin and immunoglobulins, and has essentially no impact on the concentration of growth factors others than PDGF and VEGF, such as TGF-β1, EGF, and IGF.

Further, the method of the invention allows the dissolution of lipid membranes, therefore inactivating lipid-enveloped viruses, and other pathogens like, for instance, bacteria and parasites such as protozoae, as well as the removal of plasma and platelet lipids which are present in the starting platelet concentrate. The method of the present invention thus renders it possible to provide virally-inactivated platelet-derived growth factors mixtures, which could be efficiently standardized for use in therapeutic treatments, cell therapy or cell culture.

Finally, considering the fact that, in part due to the risk of bacterial contamination and loss of functional activity for hemostasis, platelets usually have a limited shelf life of 5 or 7 days, when clinically used intravenously for the correction of quantitative or functional thrombocytopenia, a high number of platelet units older than 5 or 7 days are usually discarded each year. In allowing expired platelets stocks to be used for the preparation of platelet-derived concentrates, the method of the invention finally reveals an extremely promising economical interest.

SUMMARY OF THE INVENTION

An object of the present invention is a method for preparing a virally-inactivated growth factors-containing platelet lysate depleted of PDGF and VEGF and comprising the steps of contacting a starting platelet concentrate with a solvent and/or a detergent, incubating said starting platelet concentrate with the solvent and/or detergent for a period of at least 5 minutes to 6 hours, at a pH maintained in a range from about 6.0 to about 9.0, and at a temperature within the range of from 2° C. to 50° C., preferably within the range of from 25° C. to 40° C., removing the solvent and/or the detergent by oil extraction for obtaining an aqueous protein phase, and incubating the said aqueous protein phase with charcoal, or by removing the solvent and/or the detergent by incubating the solvent and/or detergent-treated platelet concentrate with charcoal only.

In one embodiment, the solvent used in the method of the invention is selected in the group consisting of di or trialylphosphates with different alkyl chains, and is preferably the tri-n-butylphosphate (TnBP).

In another embodiment, the detergent used in the method of the invention is selected in the group consisting of polyoxyethylene derivatives of fatty acids, partial esters of sorbitol anhydrides, non-ionic detergents, sodium deoxycholate and sulfobetaines, and more preferably in the group consisting in TRITON X-45®, TRITON X-100®, TWEEN 80®, and TWEEN 20®.

In yet another embodiment, the concentration of each of said solvent and/or of said detergent during the incubation step of the platelet concentrate with the solvent/detergent ranges from 0.2 to 5%, preferably from 0.2 to 2% in volume with respect to the volume of the starting platelets concentrate. In a preferred embodiment of the method of the invention, the starting platelet concentrate is contacted either with 2% TnBP only, or with 1% TnBP and 1% TRITON X-45®, based on the volume of the platelet concentrate.

Further, in another embodiment of the present invention, oil extraction is performed with a pharmaceutical grade oil, the oil being used in an amount of from 2 to 20 weight %, or from 5 to 15 weight % or from 5 to 10 weight %, based on the weight of the mixture of the platelet concentrate with the solvent and/or the detergent.

In another embodiment, when oil extraction is performed before incubation with activated charcoal, activated charcoal is used in an amount of from 50 to 250 g/l, preferably from 55 to 200 g/l, or from 60 to 150 g/l, or from 65 to 100 g/l of an aqueous protein phase recovered after oil extraction.

In another embodiment, when no oil extraction is performed before incubation with activated charcoal, activated charcoal is used in an amount of from 250 to 1250 g/l, preferably from 275 to 1000 g/l, or from 300 to 750 g/l, or from 325 to 500 g/l of the platelet concentrate once treated with the solvent and/or the detergent.

In one embodiment, the method of the invention comprises an additional step of centrifugation after oil extraction, and/or after incubation with charcoal.

The method of the invention may further possibly comprises an additional step consisting in chromatographying, nanofiltrating (for removal of pathogenic agents) and/or ultrafiltrating the resulting platelet lysate.

In one embodiment, the method of the invention comprises a preliminary step of preparing a starting platelet concentrate, said starting platelet concentrate being prepared by apheresis or by buffy-coat isolation from whole blood, and being either fresh, expired and stored liquid or expired and stored frozen.

Another object of the present invention is a virally-inactivated growth factors-containing platelet lysate depleted of PDGF and VEGF, or a virally-inactivated growth factors-containing platelet lysate depleted of PDGF and VEGF obtained by the method of the invention.

In one embodiment, this platelet lysate comprises the growth factors TGF-β, IGF, and EGF. In another embodiment, this platelet lysate further comprises bFGF.

In another embodiment, the virally-inactivated growth factors-containing platelet lysate according to the invention comprises:

a level of PDGF-AB lower than 10, more preferably lower than 5, more preferably lower than 3 ng/ml of said lysate; and/or a level of VEGF lower than 0.1, more preferably lower than 0.01 ng/ml of said lysate; and/or a level of TGF-β higher than 50, more preferably higher than 100, more preferably higher than 150, more preferably higher than 200, more preferably higher than 250 ng/ml of said lysate; and/or a level of EGF higher than 0.5, more preferably higher than 1, more preferably higher than 1.5, more preferably higher than 2, more preferably higher than 2.5 ng/ml of said lysate; and/or a level of IGF higher than 20, more preferably higher than 50, more preferably higher than 100 ng/ml of said lysate.

Another object of the present invention is the use of the virally-inactivated growth factors-containing platelet lysate depleted of PDGF and VEGF obtained by the method of the invention or of the virally-inactivated growth factors-containing platelet lysate depleted of PDGF and VEGF of the invention for promoting bone regeneration or reconstruction, or for treating a fractured bone.

Another object of the present invention is the use of the virally-inactivated growth factors-containing platelet lysate depleted of PDGF and VEGF obtained by the method of the invention or of the virally-inactivated growth factors-containing platelet lysate depleted of PDGF and VEGF of the invention for in vitro or ex vivo cell culture, and preferably for promoting the proliferation and/or the differentiation of stem cells. In a preferred embodiment, the growth factors-containing platelet lysate of the invention is used for promoting the differentiation of stem cells towards osteoblast lineage and/or chondrocytes.

BRIEF DESCRIPTION OF THE DRAWINGS

The foregoing and other objects and advantages of the invention and the manner in which the same are accomplished will become clearer based on the following detailed description taken in conjunction with the accompanying drawings in which.

DETAILED DESCRIPTION

The present invention will now be described more fully hereinafter with reference to the accompanying drawings, in which one embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

An object of the present invention is a method for preparing a virally-inactivated growth factors-containing platelet lysate depleted of PDGF and VEGF comprising the steps of contacting a starting platelet concentrate with a solvent and/or a detergent, incubating said starting platelet concentrate with the solvent and/or detergent for a period of at least 5 minutes to 6 hours, at a pH maintained in a range from about 6.0 to about 9.0, and at a temperature within the range of from 2° C. to 50° C., removing the solvent and/or the detergent by oil extraction for obtaining an aqueous protein phase, and incubating said aqueous protein phase with charcoal, or by removing the solvent and/or the detergent by incubating the solvent and/or detergent-treated platelet concentrate with charcoal only.

As used in the present invention, by the expression "virally-inactivated", it is meant that the growth factors-containing platelet lysate is substantially free of infectious virus, and more particularly of lipid-enveloped virus, such as for instance the human immunodeficiency virus (HIV), the hepatitis B virus (HBV), the hepatitis C virus (HCV, the West Nile virus (WNV), the TT virus, the Dengue virus, the cytomegalovirus (CMV), the Epstein Barr virus (EBV), the Human Herpes virus-8 (HHV-8), the simian foamy virus, the Severe Acute Respiratory Syndrome virus (SARS coronavirus), the H1NI and other flu viruses, as well as other lipid-enveloped such as retroviruses, hepatitis viruses, cytomegaloviruses, lactic dehydrogenase viruses, herpes group viruses, rhabdoviruses, leukoviruses, myxoviruses, alphaviruses, arboviruses, paramyxoviruses, arenaviruses and coronaviruses. By "substantially free", it is meant that the platelet growth factors preparation has an extent of inactivation of virus at least greater than 4 $\log_{10}$ as required to characterize robust viral reduction steps, by the Committee for proprietary medicinal products (CPMP) of the European Agency for the Evaluation of Medicinal Products (EMEA) in its "Note for guidance on virus validation studies" (Reference CPMP/BWP/268/95), and preferably greater than 5 $\log_{10}$ or even 6 $\log_{10}$, and is therefore unlikely to be responsible for transmission to patients of blood-borne infection due to lipid enveloped viruses.

As used in the present invention, by the term "depleted of PDGF and VEGF", it is meant that the growth factors-containing platelet lysate is substantially free of PDGF (Platelet derived growth factor) and of VEGF (vascular endothelial growth factor).

In a particular embodiment, the concentration of PDGF-AB in the virally-inactivated growth factors-containing platelet lysate according to the invention is lower than 10 ng/ml of lysate, preferably lower than 5 ng/ml of lysate, even preferably lower than 3 ng/ml of lysate.

In a particular embodiment, the concentration of VEGF in the virally-inactivated growth factors-containing platelet lysate according to the invention is lower than 0.1 ng/ml of lysate, preferably lower than 0.01 ng/ml of lysate.

As used in the present invention, "activated charcoal", "activated carbon" or "charcoal", refers to a form of carbon that has been processed to render it extremely porous. Activated charcoal thus possesses a very large surface area, providing very important adsorption capability. Activated charcoal is generally produced from carbonaceous source materials like nutshells, peat, wood, coir, lignite, coal and petroleum pitch. It can be obtained by various processes comprising physical reactivation (a precursor is developed into activated charcoal using gases) and chemical activation (the raw material is impregnated with certain chemicals such as an acid, strong base, or a salt, prior to carbonization).

The activated charcoal can be used as bulk or packed in commercially available filtration cartridges In one embodiment, the activated charcoal for use in the present invention is a powdered activated charcoal obtained by steam and/or chemical treatment. The porosity of the charcoal can be microporosity (<10 nm pore size range), mesoporosity (10-25 nm pore size range) or macroporosity (>25 nm pore size range), or a combination thereof. Different sources and the type of treatment may influence the type of porosity that is eventually obtained.

In another embodiment, the grade and/or porosity of the activated charcoal are suitable for retaining solvent, detergent, PDGF and VEGF. Activated charcoals suitable for use in the method of the present invention may originate from various suppliers, such as, for instance, in the case of pre-packed charcoal filtration cartridges, 3M®/CUNO® (activated charcoal from CUNO) and Pall (activated charcoal AKS).

When using activated charcoals from 3M/CUNO, (porosity) grade 5 activated charcoal is preferred. Further, removal of solvent, detergent, PDGF and VEGF is more efficient with porosity 5 of grade 5 3M®/CUNO® activated charcoal than with porosities 2, 3 and 4. Similarly, when using activated charcoal from Pall, AKS grade 6 is preferred to AKS 7 and 4, since it provides a better removal of solvent, detergent, PDGF and VEGF.

In one embodiment, the activated charcoal for use in the method of the invention is capable to adsorb methylene blue in a range of from 100 to 550, and in one embodiment from 300 to 500 g/m$^2$ or in another embodiment 100 to 300 g/m$^2$ (methylene blue is currently used a standard substance for measuring adsorption capacity of activated charcoal). The charcoal may also be selected depending on the viscosity of the fluid to be treated; charcoal designed for low viscosity fluids (e.g. with a viscosity below 20 cp) is preferred.

One specific charcoal that can be used is CUNO R55, where the first 5 indicates the filtration rating (linked to the viscosity) and the second 5 indicated the carbon grade.

By the expression "removing the solvent and/or the detergent", it is meant that the level of solvent and/or detergent in the virally-inactivated growth factors-containing platelet lysate is extremely low, and preferably undetectable. It is indeed well-known from the skilled person in the art that elevated concentrations in solvent and/or detergent are directly linked with long-term toxicity, and more particularly with the onset of neurological conditions (such as disclosed in J. P. R. Pelletier, S. Transue, E. L. Snyder. Pathogen inactivation techniques. Best Practice & Research Clinical Haematology Vol. 19, No. 1, pp. 205-242, 2006).

Therefore, by the expression "extremely low" concerning the solvent, it is meant in the present invention that the solvent level is of less than 100 ppm, preferably less than 50 ppm, preferably less than 20 ppm, more preferably less than 10 ppm, less than 5 ppm, and even more preferably less than 1 ppm.

Further, by the expression "extremely low" concerning the detergent, it is meant in the present invention that the detergent level is of less than 500 ppm, preferably less than 250 ppm, more preferably less than 100 ppm, more preferably less than 50 ppm, and even more preferably less than 10 ppm.

The virally-inactivated growth factors-containing platelet lysate according to the invention or obtained by the method of the invention comprises at least the following functional growth factors: the transforming growth factor (TGF-β) superfamily, comprising, among others, TGF-β1 and/or TGF-β2, the insulin-like growth factor (IGF) and the epidermal growth factor (EGF). In a preferred embodiment, the growth factors-containing platelet lysate of the invention further comprises the basic fibroblast growth factor (bFGF).

In a particular embodiment, the concentration of TGF-β1 in the virally-inactivated growth factors-containing platelet lysate according to the invention is at least similar to that of the starting platelet concentrate, and preferably higher than 50, preferably higher than 100, preferably higher than 150, preferably higher than 200, preferably higher than 250 ng/ml of the lysate.

In a particular embodiment, the concentration of IGF in the virally-inactivated growth factors-containing platelet lysate according to the invention is at least similar to that of the starting platelet concentrate, and preferably higher than 20, preferably higher than 50, preferably higher than 100 ng/ml of the lysate.

In a particular embodiment, the concentration of EGF in the virally-inactivated growth factors-containing platelet lysate according to the invention is higher than 0.5, preferably higher than 1, preferably higher than 1.5, preferably higher than 2 and preferably higher than 2.5 ng/ml of the lysate.

In a particular embodiment, the virally-inactivated growth factors-containing platelet lysate of the invention or obtained by the method of the invention does not lead to blood cell-related transfusion reactions. By "blood cell-related transfusion reactions", it is meant that this virally-inactivated growth factors-containing platelet lysate is free of intact living cells (such as red cells, platelets and white blood cells, for instance) and therefore allows to avoid a range of well-known transfusion reactions, including immunological (such as alloimmunization) and hemolytic complications, in patients (see, for instance Stroncek et Rebulla, "Platelet transfusions", The Lancet, Aug. 4, 2007; vol. 370: 427-438). Indeed, a recipient who is immunocompetent often exhibits an immune response to the donor blood cell antigens, thus resulting in a variety of clinical consequences depending on the blood cells and specific antigens involved. The antigens most commonly involved are selected in the following categories: (1) HLAs class I, which are shared by platelets and leukocytes, (2) HLAs class II, which are present on some leukocytes, (3) granulocyte-specific antigens, (4) platelet-specific antigens (such as, for instance, human platelet antigen HPA), and (5) Red Blood Cells-specific antigens.

In a particular embodiment, the virally-inactivated growth factors-containing platelet lysate of the invention is prepared from platelet concentrates collected from AB blood group donors and is thereby free of anti-A or anti-B hemagglutinins, thereby avoiding in particular potential haemolytic reactions in recipients.

In another particular embodiment, the virally-inactivated growth factors-containing platelet lysate of the invention is prepared from typed platelet concentrates collected from isogroup blood donors (for instance group A or group B donors) to be used in patients of the same blood group as the donors.

More specifically, as regards the preparation method of the invention, living blood cells (red blood cells, white blood cells, and platelets) are destroyed/lysed by the solvent-detergent treatment, thereby reducing, and preferably preventing, the risk of exposing the patient to foreign antigens and intact blood cells. The method of the invention thus allows to prepare a virally-inactivated growth factors-containing platelet lysate either from platelets obtained from the patient to be treated itself or from allogeneic platelets.

In another embodiment, the virally-inactivated growth factors-containing platelet lysate obtained by the method of the invention further comprises immunoglobulins such as IgG, IgM, and/or IgA.

In a particular embodiment, the concentration of immunoglobulin IgG in the virally-inactivated growth factors-containing platelet lysate according to the invention is preferably higher than 5 g/L of the lysate, and preferably about 8 g/L of the lysate.

In another embodiment, the virally-inactivated growth factors-containing platelet lysate obtained by the method of the invention can be further subjected to additional purification steps such as ion-exchange chromatography in order to remove immunoglobulins such as IgG, IgM, and/or IgA.

In another embodiment, the virally-inactivated growth factors-containing platelet lysate of the invention or obtained by the method of the invention comprises at least one of albumin, fibrinogen and prothrombin.

In a particular embodiment, the concentration of albumin in the virally-inactivated growth factors-containing platelet lysate according to the invention is preferably higher than 30 g/L of the lysate.

In another embodiment, the virally-inactivated growth factors-containing platelet lysate of the invention or obtained by the method of the invention further comprises α1-antitrypsin, α2-antiplasmin, α2-macroglobulin, transferrin, fibronectin and C1-INH.

In a preferred embodiment, the incubation of the platelet concentrate with the solvent and/or detergent performed in the method of the invention ranges from 2 to 4 hours, at a physiological pH, e.g. a pH ranging from pH 7.0 to pH 7.5 (when starting platelets are fresh platelets) or at a pH ranging from pH 6.8 to 8.2 (when starting platelets are expired and/or frozen platelets). Advantageously, the incubation temperature is about 31° C.

Suitable solvents for use in the method of the invention are di- or trialkylphosphates, such as tri-(n-butyl)phosphate, tri-(t-butyl)phosphate, tri-(n-hexyl)phosphate, tri-(2-ethylhexyl)phosphate, tri-(n-decyl)phosphate, di-(n-butyl)phosphate, di-(t-butyl)phosphate, di-(n-hexyl)phosphate, di-(2-ethylhexyl)phosphate, di-(n-decyl)phosphate as well as dialkylphosphates with different alkyl chains. Di or trialkylphosphates having different alkyl chains can be employed, for example ethyl di-(n-butyl)phosphate. An especially preferred trialkylphosphate is tri-(n-butyl)phosphate (TnBP).

Suitable detergents for use in the method of the invention include polyoxyethylene derivatives of fatty acids, partial esters of sorbitol anhydrides, for example the products commercialized under the names "TWEEN 80®" also known as "polysorbate 80", "TWEEN 20®", and non-ionic detergents, such as oxyethylated alkylphenol sold under the name "TRITON X-100®" or "TRITON X-45®". Further contemplated detergents are sodium deoxycholate and sulfobetaines, such as N-dodecyl-N, N-dimethyl-2-ammonio-1-ethane sulphonate. Especially preferred detergents are "TRITON X-45®", "TRITON X-100®", "TWEEN 80®", and "TWEEN 20®".

In a particular embodiment of the invention, the starting platelets concentrate is incubated with a solvent and a detergent, preferably TnBP and TRITON X-45®.

Advantageously, the final concentration of the solvent or of the detergent, or of each one of the solvent and the detergent, is comprised in a range of from 0.2 to 5%, preferably from 0.2 to 2% in volume with respect to the volume of the platelet concentrate. In a preferred embodiment, the starting platelet concentrate is incubated with 2% TnBP. In another preferred embodiment, the starting platelet concentrate is incubated with 1% TnBP and 1% TRITON X-45®.

The solvent and/or detergent can be extracted from the biological fluid by oil extraction with pharmaceutical grade oil and by charcoal extraction, or by charcoal extraction only, such that the remaining lysate is depleted in solvent and/or detergent.

The pharmaceutical grade oil can be a naturally occurring oil, for example extracted from a plant or an animal, or a synthetic compound of similar structure. Suitable naturally occurring oils include castor oil (also known as ricinus oil), soybean, sunflower oil, cottonseed oil. A preferred synthetic compound is a synthetic triglyceride. Examples of suitable synthetic triglycerides include triolein, tristearin, tripalmitin, trimyristin, and combinations thereof.

The amount of pharmaceutical grade oil is the amount that allows the extraction of at least 80% of lipid soluble process chemicals, the oil being used in an amount of from 2 to 20 weight %, based on the weight of the platelets concentrate, preferably from 5 to 15 weight % and more preferably from 5 to 10 weight %.

The charcoal extraction can be performed with any of the above mentioned activated charcoals, provided said charcoals allow adsorbing and retention of solvent and/or detergent particles. The charcoal extraction can be performed in batch (i.e. the charcoal is mixed with the aqueous protein phase recovered after oil extraction) or in column (the aqueous protein phase is then passed on preferably sedimented charcoal), or through pre-packed commercial cartridges. In a preferred embodiment, the charcoal extraction is performed in batch.

In a preferred embodiment, when oil extraction is performed before incubation with activated charcoal, charcoal extraction is performed with activated charcoal in an amount of from 50 to 250 g/l, preferably from 55 to 200 g/l, or from 60 to 150 g/l, or from 65 to 100 g/l of said aqueous protein phase. In a further preferred embodiment, the charcoal extraction is performed with activated charcoal in an amount of 75 g/l of the aqueous protein phase recovered after oil extraction.

In another embodiment, when no oil extraction is performed before incubation with activated charcoal, charcoal extraction is performed with activated charcoal in an amount of from 250 to 1250 g/l, preferably from 275 to 1000 g/l, or from 300 to 750 g/l, or from 325 to 500 g/l of the solvent and/or detergent treated platelet concentrate.

In another embodiment, the level of solvent after oil and charcoal extraction or after charcoal extraction only is of less than 100 ppm, preferably less than 50 ppm, preferably less than 20 ppm, more preferably less than 10 ppm, less than 5 ppm, and even more preferably less than 1 ppm.

In one embodiment, the level of detergent after oil and charcoal extraction or after charcoal extraction only is of less than 500 ppm, preferably less than 250 ppm, more preferably less than 100 ppm, more preferably less than 50 ppm, and even more preferably less than 10 ppm.

In a particular embodiment, the method of the invention may further comprise at least one step of centrifugation after oil extraction, or after incubation with charcoal. Preferably, the centrifugation step performed after oil and charcoal extraction or charcoal extraction only allows removing cell debris. Advantageously, the centrifugation step is performed at 800 to 20000×g. for 10 to 30 minutes, and preferably at 10000×g. for 15 minutes.

In one embodiment, the method of the invention may also further comprise at least one additional step selected from a chromatographic purification and/or an ultrafiltration, and/or a nanofiltration, and/or sterile filtration.

The possible chromatographic purification is then carried out subsequently to oil and charcoal extraction or to charcoal extraction. Preferably, the mixture of charcoal and of the aqueous protein phase recovered after oil extraction, or of charcoal and of the solvent and/or detergent-treated platelet concentrate is centrifuged after incubation. The supernatant is collected and loaded on the chromatographic support in particular to fractionate the components of the mixture or to remove some components.

Suitable chromatography columns that can be used comprise reversed-phase (hydrophobic interaction) matrices, or protein adsorption matrices such as ion-exchange (anion and cation) matrices and affinity (such as immuno-affinity or immobilized heparin) matrices, or size-exclusion matrices. In a preferred embodiment, the growth factors contained in the platelet lysate are retained on the chromatographic supports used, and further eluted with a suitable elution buffer. Preferably, the chromatographic conditions are selected such as to allow performing the chromatographic separation/purification at a pH which is compatible with the stability and the physiological function of the growth factors of interest, for instance a substantially neutral pH such that denaturation of the growth factors could be avoided. The loading, washing and eluting conditions are determined according to the general knowledge of the skilled person in the art.

Following the solvent and/or detergent removal by oil and charcoal extraction or by charcoal extraction only, a further step might be added to inactivate or remove non-enveloped viruses, such as parvovirus B19 or, possibly, hepatitis A virus (HAV), for example by nanofiltration and more particularly by nanofiltration using 75-nm, 35-nm, 20-nm, 15-nm, or 10-nm pore size filter membrane.

In a particular embodiment, the platelet concentrate used as starting material in the method of the invention corresponds to single or pooled standard platelet concentrates, for example platelet concentrates which were prepared for transfusion. The platelet concentrate may also originate from whole blood buffy-coat isolation. One unit of buffy-coat derived platelet concentrate generally corresponds to 30 to 50 ml. Buffy coat derived platelets may be used as starting material either as a single unit or as a pool of single units, for instance under the form of a therapeutic unit, corresponding to a pool of 4 to 6 single units (as disclosed in the Guide to the preparation, use and quality assurance of blood components—13th edition (2007), edited by the Council of Europe.

The platelet concentrate may also be obtained by apheresis, cytapheresis or plateletpheresis standard procedures (see for instance the Guide to the preparation, use and quality assurance of blood components, $13^{th}$ edition (2007), edited by the Council of Europe), and may be obtained using MCS+ (HAEMONETICS®), TRIMA ACCELL® or COBE® Spectra (GAMBRO®) or AMICUS® (BAXTER®). An apheresis procedure generally yields a larger volume per donor (corresponding to a 300 ml platelet concentrate), when compared to that obtained through buffy-coat isolation procedures.

In one embodiment, the method of the invention comprises a preliminary step consisting in preparing a starting platelet concentrate. Advantageously, methods for preparing a starting platelet concentrate include, but are not limited to, standard blood bank procedures such as apheresis or platelet preparation from whole blood donations, and point-of-care procedures, such as those using blood cell savers/separators or table top devices.

The platelet concentrate used as starting material in the method of the invention may be fresh, i.e. less than 5 or 7 days after collection, expired, i.e. more than 5 or 7 days after collection, or expired and frozen for several weeks at −20° C. or colder.

In a particular embodiment, the platelet concentrate used as starting material for the method of the invention may further comprise white blood cells and/or red blood cells. The starting platelet concentrate may therefore comprise several differentiated and nonactivated leukocytes such as lymphocytes, neutrophilic granulocytes, and monocytes. Neutrophils and monocytes, in particular, are rich in granules containing myeloperoxidase, which catalyzes the oxidation of chloride to generate hypochlorous acid and other reactive oxygen derivates that act as potent bactericidal oxidants toxic to microorganisms and fungi.

Therefore, when the starting platelet concentrate comprise several differentiated and nonactivated leukocytes, the virally-inactivated growth factors-containing platelet lysate obtained by the method of the invention further comprises antimicrobial components as well as various growth factors originating from the leukocytes.

In a particular embodiment, leukocytes are eliminated from the platelet concentrate used as starting material, preferably by leukoreduction, such that the proinflammatory effects of the proteases and acid hydrolases contained in white blood cells is avoided. Leukoreduction also allows to reduce the risk of a possible prion contamination.

A normal platelet count in a healthy person is generally comprised between 150000 and 400000 platelets per $mm^3$ of blood, i.e. 150 to $400 \times 10^9$ platelets/L. This "normal" platelet count is found in about 95% of healthy people, while the remaining 5% may have a statistically abnormal platelet count (either very low or very high).

When platelets are collected by apheresis, the platelet count is generally higher than $1.2 \times 10^9$ platelets per ml for a bag of 250 ml, thereby corresponding to a platelet count of more than about $3 \times 10^{11}$ platelets per bag (unit).

In one embodiment, the number of platelets in the starting platelet concentrate is 3 to 10 times higher than that usually found in blood.

The virally-inactivated growth factors-containing platelet lysate of the invention or obtained by the method of the invention may be mixed with artificial scaffolds, such as those made of collagen, chitosan, ceramics for instance, or with plasma derived fibrin glues or fibrin sealants, such as to be used for therapeutic purpose, i.e. for a curative or prophylactic treatment for treating conditions in human and/or animals, for restoring, correcting or modifying the physiological functions thereof through a pharmacological, immunological or metabolic effect.

The virally-inactivated growth factors-containing platelet lysate of the invention or obtained by the method of the invention is especially suitable for treating conditions in human and/or animals an/or for contacting superficial parts of the body thereof since it is both cleared of solvent and/or detergent, and virally safe.

Additional compounds may also be added to the virally-inactivated growth factors-containing platelet lysate, which comprise, but are not limited to, chemotherapeutic agents, antibiotics and/or hormones.

Another object of the invention is the use of the virally-inactivated growth factors-containing platelet lysate of the invention or obtained by the method of the invention in therapeutic application, as well as for in vitro or ex vivo cells culture. When used for in vitro or ex vivo cells culture, the virally-inactivated growth factors-containing platelet lysate of the invention or obtained by the method of the invention is present in the culture medium in the range of from 1% to 30%, preferably, from 2% to 20% and more preferably from 3% to 10% with respect to the volume of the culture medium.

Another object of the invention is a pharmaceutical and/or a cosmetic product comprising the virally-inactivated growth factors-containing platelet lysate of the invention or obtained by the method of the invention.

By "pharmaceutical product", it is meant a platelet gel, a platelet glue, a growth factors-enriched fibrin glue and/or sealant, artificial scaffolds.

By "cosmetic product", it is meant any of several preparations applied to the human body for beautifying, preserving, or altering the appearance or for cleansing, colouring, conditioning, or protecting the skin, hair, nails, lips, eyes, or teeth.

Another object of the invention is the use of the virally-inactivated growth factors-containing platelet lysate of the invention or obtained by the method of the invention in a culture medium which is suitable for in vitro or ex vivo culturing of fibroblasts, chondrocytes, osteoblasts, keratinocytes, stem cells and/or transplants cells. Another object of the invention is a culture medium suitable for in vitro or ex vivo culturing of fibroblasts, chondrocytes, osteoblasts, keratinocytes, stem cells and/or transplants cells, and containing the virally-inactivated growth factors-containing platelet lysate of the invention or obtained by the method of the invention.

In a particular embodiment, the use of the virally-inactivated growth factors-containing platelet lysate of the invention promotes the propagation and/or the differentiation of stem cells, in particular of Mesenchymal Stem cells (MSC). In a preferred embodiment, the use of the virally-inactivated growth factors-containing platelet lysate of the invention promotes the differentiation of stem cells towards osteoblast or chondrocyte lineage.

Another object of the present invention is the use of the virally-inactivated growth factors-containing platelet lysate depleted of PDGF and VEGF of the invention for promoting bone reconstruction, bone regeneration or wound healing, as well as for cosmetic use The above and other objects, features and advantages of the present invention will become more apparent from the following description, reference being made to the accompanying figures.

EXAMPLES

I—Material and Methods

1—Apheresis Platelet Collection

Starting platelet concentrates (PCs) were collected from volunteer donors after informed consent using a MCS+ multiple component system (HAEMONETICS®, Braintree, USA). Whole blood was withdrawn through a venous catheter, using an intermittent flow, and immediately anticoagulated at a 1/9 ratio with citrate dextrose solution Formula A. The platelets were separated from erythrocytes and other blood components by continuous centrifugation, suspended in plasma and collected into a sterile container. Several separation cycles were performed until the total volume of PC collected reached a volume range between 225 and 315 mL and a predefined platelet yield target equal to or greater than $3.0 \times 10^{11}$. PCs were stored under slow mixing at room temperature and were processed within 24 to 72 hours of collection.

2—Cell Counts

The content in red blood cells, platelets, and white blood cells in the starting PC was determined using a cell counter (ABC Vet automatic blood counter, ABX Diagnostics®, Montpellier, France).

Figure 1:
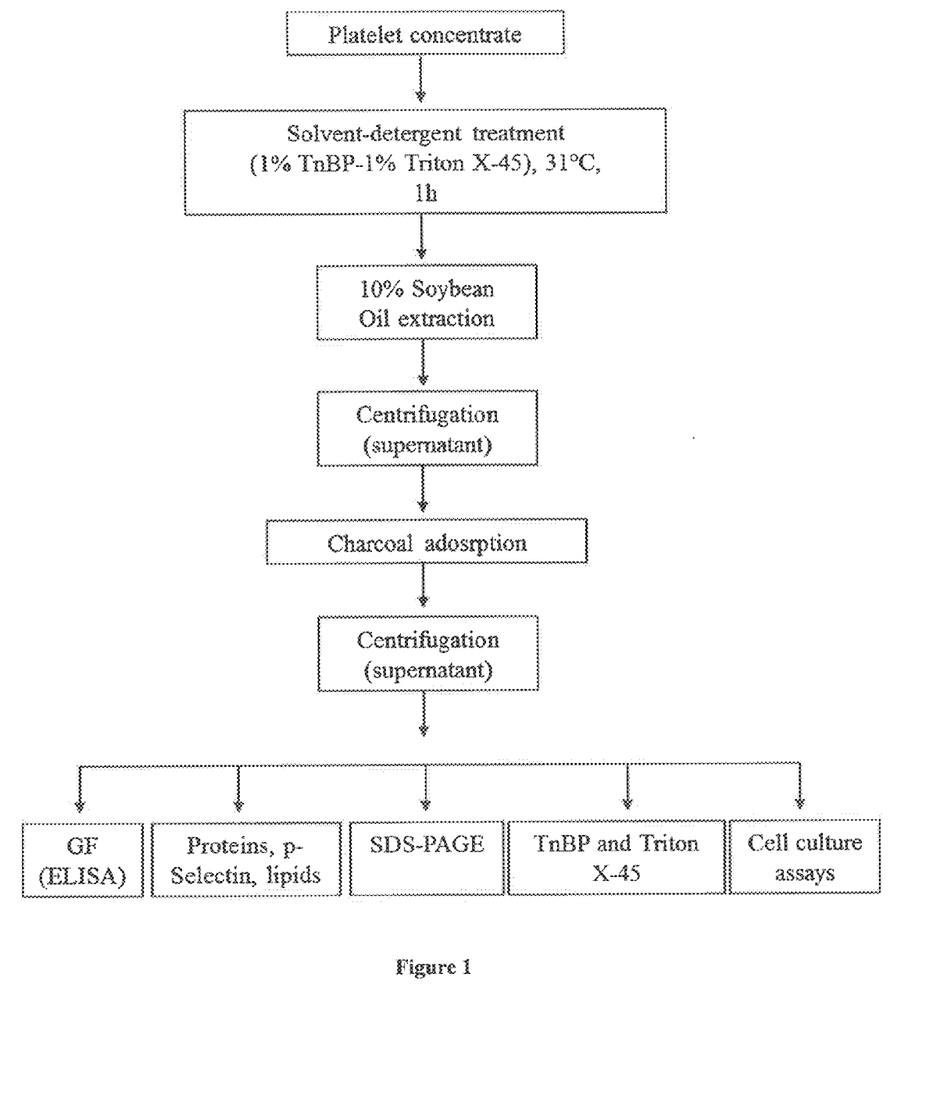
FIG. 1 depicts the preparation process of the growth factor mixture enriched in TGF-β1 and depleted in PDGF-AB and VEGF.

3—Processing of Starting Platelet Concentrates a—Study Design:

Starting platelets concentrates were processed according to the study design in FIG. 1.

Briefly, the PC (300 mL) was transferred into a plastic bag and processed as described in EP 1 685 852. Plasma concentrates were incubated with a combination of 1% (final concentration) (v/v) tri-n-butyl phosphate (TnBP; MERCK© KGaA, Darmstadt, Germany) and 1% (final concentration) (v/v) TRITON X-45® (SIGMA®, Missouri, USA), at room temperature (RT) for 1 hr under constant gentle stirring (70 rpm; FINEPCR®, Seoul, Korea).

10% (v/v; final concentration) of soybean oil (SIGMA®, Missouri, USA) was then added and mixed first vigorously for 30 seconds then at 70 rpm with the S/D-treated PC (S/D-PC) for 15 min at room temperature (RT).

The oil/S/D-PC mixture was then decanted for 45 min to separate a clear oily phase (top), a turbid phase (intermediate) and a clear aqueous protein phase (bottom).

The aqueous protein phase (about 270 mL) was recovered by gravity from the bottom of the bag and clarified by centrifugation at 6000×g for 10 min at 20-25° C. to pellet any cell debris or insoluble material.

After centrifugation, the supernatant (S/D-PC-O; about 265 mL) was recovered and mixed for 30 min at 70 rpm and RT with 19.9 g of activated charcoal (3M®, St. Paul, Minn., USA) corresponding to a ratio of 1.5 g/20 mL of S/D-PC-O. The mixture was then centrifuged (6000×g; 10 min, RT) to pellet the charcoal and recover a clear supernatant (S/D-PC-OC). Samples were taken along the process and frozen at −80° C. until analysis. The data presented are average figures from four or five repetitions.

4—Impact of Charcoal Ratio

Preliminary small-scale experiments were performed to determine the optimal quantity of charcoal to be used to remove TnBP and TRITON® X-45 and evaluate the impact on GF and protein content. Increasing amount of charcoal (1.5 to 4 g) was mixed with the S/D-PC-O (20 mL) for 30 min, RT, and 70 rpm using a rotating mixer. The mixtures were then centrifuged (6000×g; 10 min, RT) to pellet the charcoal and recover the clear supernatant which was frozen at −30° C. till assessment.

5—Growth Factors Assays 1-ml samples were taken at each step of the procedures. They were centrifuged at 10000×g for 15 min (MICROFUGE® 22R, Beckman Coulter, Fullerton, Calif.) to pellet the platelets and/or cell debris and obtain cell-free supernatants for platelet-derived growth factors measurements. Supernatants were then immediately frozen at −80° C.

Samples were thawed at 37° C. and analyzed within 1 h by sensitive and specific commercially available immunoassays. Standards and samples were assayed in duplicate, and mean values were calculated. The results were multiplied by the dilution factor applied to the samples.

PDGF-AB, TGF-β1, EGF, VEGF, and IGF-1 were in particular measured by ELISA assay using QUANTIKINE® kits (R&D Systems®; Minneapolis, Minn.).

a—PDGF-AB

PDGF-AB was assayed using the QUANTIKINE® ELISA kit (#.DHDOOB, R&D SYSTEMS®, Minneapolis, Minn.). Samples were diluted 100 times in the Calibrator Diluent (RD6-11). The plates were incubated for 2 h, washed, and incubated with enzyme conjugated antibodies to PDGF-AB for an additional 3 h at room temperature. The wells were washed using the Wash Buffer, then the Substrate Solution was added for 20-30 min at room temperature. Wells were protected from light. Stop Solution was added to each well, and the absorptions at 450 nm were determined using a microtiter plate reader. The minimum detectable dose was 1.7 pg/ml.

b—TGF-β1

TGF-β1 was determined by using the QUANTIKINE® ELISA kit (DB100B, R&D SYSTEMS®) Samples were diluted 100-fold in the Calibrator Diluent (RD5-26). A dilution series of TGF-β1 standards (890207) was prepared in 100-μl volumes in 96-well microtiter plates coated with TGF-β-receptor II. Before analysis of TGF-β1, acid activation and neutralization was performed to activate latent TGF-β1 to the immunoreactive form. For this purpose, 0.5 ml samples were mixed with 0.1 ml of 1N HCl, incubated at room temperature for 10 min, neutralized by an addition of 0.1 ml of 1.2N NaOH/0.5M HEPES (N-[2-hydroxyethyl]piperazine-N0-[2-ethanesulfonic acid]) from Sigma (H-7523), and centrifuged. The supernatant fraction was then assayed for total TGF-β1 content. Aliquots (50 μl) were applied in duplicate to the microtiter plate, which was then covered and incubated for 2 h at room temperature. The wells were then washed, enzyme-conjugated polyclonal antibody to TGF-b1 was added, and incubation continued for 1.5 h at room temperature. Measurements were completed as described above. The detection limit of TGF-β1 was 4.61 pg/ml.

c—EGF

EGF was assayed using the QUANTIKINE® ELISA kit (#.DEGOO, R&D Systems®, Minneapolis, Minn.). Samples were diluted 20-fold in Calibrator Diluent (RD6N). 200 μl of Standard, control, or sample was added in the wells. The plates were incubated for 2 h at room temperature. Each well was aspirated and washed by filling with Wash Buffer. EGF conjugate was added to each well, and incubated for 2 h at room temperature, The wells were washed using the Wash Buffer and Substrate Solution (200 μl) was added to each well. The mixture was incubated for 20 minutes at room temperature and protected from light. Stop Solution (50 μl) was added to each well. The optical density of each well was determined within 30 minutes, using a microplate reader (VERSAMAX® microplate reader, Molecular Devices, USA) set at 450 nm. The minimum detectable dose was 0.7 pg/ml.

d—VEGF

VEGF was assayed using the QUANTIKINE® ELISA kit (# DVE00, R&D Systems®, Minneapolis, Minn.). Samples were diluted 2-fold in Calibrator Diluent (RD6U). The minimum detectable dose is typically less than 9.0 pg/ml and the mean MDD was 50 ng/ml, as reported by the manufacturer. 100 μl of assay diluent (RD1W) were added to each well, followed by 100 μl of standard (VEGF standard). The plates were covered with adhesives strips and incubated for 2 h at room temperature. The wells were washed 3 times and then incubated with enzyme-conjugated VEGF for 2 h at room temperature.

e—IGF-1

IGF-1 was quantified using a QUANTIKINE® ELISA kit (DG100, from R&D Systems). Samples were diluted 100-fold in Calibrator Diluent (RD5-22). The minimum detectable dose ranged from 0.007 to 0.056 ng/ml and the mean MDD was 0.026 ng/ml, as reported by the manufacturer. 150 μl of assay diluent (RD1-53) were added to each well, followed by 50 μl of standard (890775). The plates were covered with adhesives strips and incubated for 2 h at 2-8° C. The wells were washed 3 times and then incubated with enzyme-conjugated IGF-1 for 1 h at 2-8° C. Measurements were completed as described above.

6—P-Selectin Assay

P-selectin was determined by ELISA assay using QUANTIKINE® kits (R&D Systems®).

7—Protein and Lipids Assays

Total protein, albumin, total cholesterol and triglycerides (TG) were determined in the starting PC, after the oil extraction and after charcoal adsorption by RocheP800 analyser. IgG, IgM and IgA were measured using fully automatic latex-enhanced immunoturbidimetric assays on a Cobas Integra 800 (ROCHE© COBAS INTEGRA® 800, ROCHEDIAGNOSTICS©, Mannheim, Germany).

8—Sodium Dodecyl Sulfate-Polyacrylamide Gel Electrophoresis (SDS-PAGE)

SDS-PAGE were performed under non-reduced and reduced conditions using 4-12% gradient gels, reagents, and electrophoretic systems from Invitrogen (Invitrogen Corporation, Carlsbad, Calif., USA). Molecular mass assessment was done using NOVEX®Sharp Pre-Stained Protein Molecular Weight Standard (Invitrogen).

9-TnBP and TRITON® X-45 determination

The extraction of the samples for determination of residual TnBP and TRITON® X-45 was done as described previously (19). The quantitation of TnBP was performed by gas chromatography (GC-17A, SHIMADZU©, Tokyo, Japan) and flame ionization detection, and that of Triton X-45 by high performance liquid chromatography (SHIMADZU©) using a LiChrospher 100 RP-18 column (ID: 4 mm, length: 250 mm, P/N: 724964, Merck KGaA, Darmstadt, Germany), respectively.

10—Cell Cultures

The capacity of the S/D-PC-OC to stimulate in vitro cell growth and replace FBS was evaluated using the following cell lines: (a) human osteoblasts MG63 (ATCC CRL 1427, Bioresource Collection and Research Center, BCRC, Hsingchu, Taiwan) and (b) StatensSeruminstitute rabbit corneal epithelial cells (SIRC) (ATCC CCL-60, BCRC). Maintenance of the cell lines was at 37° C. in a controlled atmosphere containing 5 percent $CO_2$. They were cultured at a density of $2 \times 10^3$ cells per well in flat bottomed 96-well plates (GREINER BIO-ONE© Tokyo, Japan) and using minimum Essential Medium (MEM; Gibco, Invitrogen) containing 2.2 g of $NaHCO_3$, 0.1 mM non-essential amino acids, 1 mM sodium pyruvate, 2 mM L-glutamine, 100 U/mL penicillin, and 100 μg/mL streptomycin, and supplemented with 10% (v/v) FBS (GIBCO®, INVITROGENT™). For the experiments, cells were first allowed to adhere for 18 hours, and were then starved for 6 hours in a serum-free medium before testing the different GF supplements. After two washes with serum-free medium, cells were cultured for up to 5 days in the medium supplemented with various concentrations (1 to 10%) of the S/D-PC-OC (corresponding to a final concentration range in TGF-β between 0.31 and 3.1 ng/ml, respectively). As controls, cell cultures without any protein/GF supplement or supplemented with 10% FBS were also carried out in each run.

11—MTS Assay

Viable cells in proliferation were determined at 5 days of culture using the MTS tetrazolium[3-(4,5-dimethylthiazol-2-yl)-5-(3-carboxymethoxyphenyl)-2-(4-sulfophenyl)-2H-tetrazolium, inner (Promega Corporation, Madison, Wis., USA) following manufacturer's instructions. This assay uses solutions of MTS and an electron coupling reagent (phenazine methosulfate) PMS. MTS is bioreduced by cells into a formazan product that is soluble in tissue culture medium. The conversion of MTS into formazan is induced by dehydrogenase enzymes present in metabolically active cells. The absorbance of formazan at 490 nm was measured from the 96-well assay plates and is directly proportional to the number of living cells in culture. After preparation, the solutions were kept in light-protected tubes at −20° C. MTS and PMS detection reagents were mixed, using a ratio of 20:1 (MTS:PMS), immediately prior to addition to the cell culture at a ratio of 1:5 (MTS+PMS/medium).

12—Statistical Analysis

Data are reported as mean+/− standard deviation (SD). Statistical comparisons were made with a two-tailed paired Student test. A p value of less than 0.05 was used to assess the significance of the differences in mean test parameters. Differences were considered significant if p<0.05.

II—Results

1—Cell Counts

The starting PC had a mean of 1216+/−188.6×$10^6$ platelets/ml (range: 896-1388×$10^6$/ml). The mean white blood cells and red blood cells counts was 0.32+/−0.10 (range: 0.20-0.4)×10/ml and 0.04+/−0.01 (range: 0.02-0.06)×10/ml, respectively. Blood cells were undetectable in all fractions subsequent to the S/D treatment.

2—Determination of the Optimal Ratio of Charcoal

Figure 2:
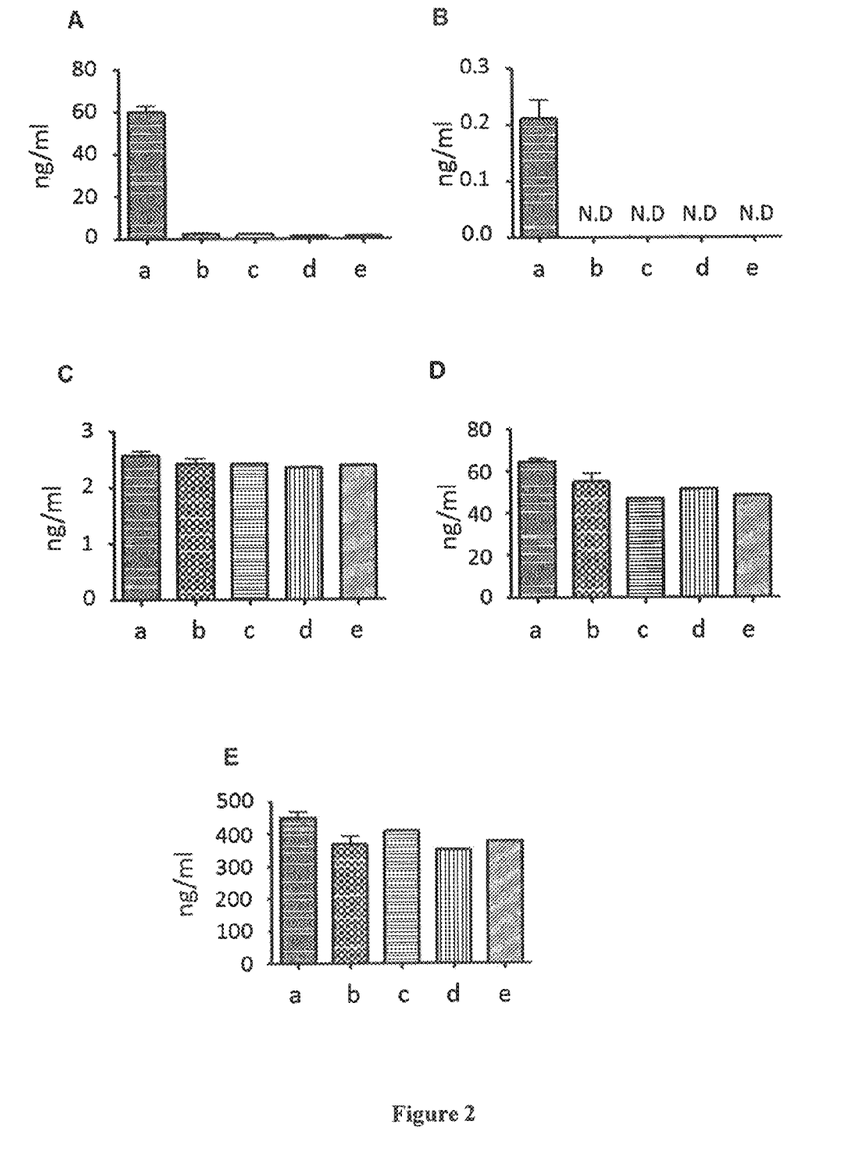
FIG. 2 represents the content in PDGF-AB (A), VEGF (B), EGF (C), IGF-1 (D), and TGF-β1 (E) in S/D-PC-O (a) and after treatment with 1.5 (b); 3 (c); 3.5 (d); and 4 (e) g of activated charcoal per 20 mL of S/D-PC-O (i.e. aqueous protein phase recovered after oil extraction)

Preliminary experiments indicated that charcoal treatment, at the various ratios tested, removed the S/D agents but also dramatically reduced the content in PDGF-AB and VEGF. Therefore tests were performed where increasing amount of charcoal (1.5; 3; 3.5; or 4 g) were mixed with 20 mL of S/D-PC-O. Residual TnBP was <2 ppm at all ratios evaluated, whereas residual TRITON® X-45 was 9, 3, 2, and 1.5 ppm, respectively. FIG. 2 shows a typical impact of charcoal treatment of a S/D-PC-O fraction on the content in PDGF-AB, TGF-β1, EGF, VEGF, and IGF-1. Concentration in TGF-β1, EGF, and IGF-1 remained essentially unchanged, whereas PDGF-AB and VEGF content was dramatically reduced at all ratios evaluated. The ratio of 1.5 g of charcoal per 20 mL of S/D-PC-O which allowed to reduce TnBP and TRITON® X-45 to less than 10 ppm was therefore selected for further experiments.

3—Composition of the Various Fractions

The impact of charcoal treatment (mean of 4 experiments) using 19.9 g of charcoal for 265 mL of a P/D-PC-O extract (corresponding to the selected ratio of 1.5 g/20 mL) on the content in GF, p-selectin, proteins, cholesterol, and TG is shown in Table 1. TGF-β1, IGF, and EGF concentration remained essentially constant after oil extraction and charcoal adsorption (about 368, 55, and 2.4 ng/mL, respectively). Mean overall recovery of the GF in S/D-PC-OC, compared to the content detected in S/D-PC-O, was 81.5, 94 and 83.8% for TGF-β1, EGF and IGF, respectively. By contrast, the mean concentration in PDGF and VEGF decreased significantly (p<0.01) during charcoal treatment (about 2.31 ng/mL and <0.009 ng/mL, respectively), confirming the observations made during the small-scale experiments. The p-selectin content was not much affected by the charcoal treatment, with only a minor decrease. The mean concentration in albumin, IgG, IgA, IgM remained essentially unchanged but a small significant decrease (p<0.05) in the content in fibrinogen was observed. The mean cholesterol and TG content remained stable. Mean TnBP was decreased from about 738 ppm down to 8.7 ppm, and TRITON® X-45 from 2628 ppm down to 8.8 ppm (p<0.001).

TABLE 1

Composition of S/D-treated platelet concentrate after oil extraction (S/D-PC-O) and after charcoal treatment (S/D-PC-OC) (N = 4)

| Parameter | S/D-PC-O | S/D-PC-OC |
|---|---|---|
| Growth factors, ng/mL | | |
| PDGF-AB | 59.9 ± 2.9 | 2.3 ± 0.52** |
| TGF-β1 | 452.0 ± 17.69 | 368.4 ± 24.6 |
| EGF | 2.56 ± 0.1 | 2.41 ± 0.1 |
| IGF | 64.5 ± 1.1 | 54.7 ± 4.1 |
| VEGF | 0.21 ± 0.03 | <0.009 |
| P-selectin | 273.9 ± 5.0 | 262.5 ± 4.3* |
| Proteins, mg/Ml | | |
| Total protein | 60.3 ± 0.5 | 60.0 ± 0.08 |
| Albumin | 38.7 ± 0.38 | 40.0 ± 0.08 |
| IgG | 8.2 ± 0.4 | 8.5 ± 0.04 |
| IgM | 0.79 ± 0.05 | 0.87 ± 0.02 |
| IgA | 1.49 ± 0.11 | 1.67 ± 0.1 |
| Fibrinogen | 4.5 ± 0.3 | 2.65 ± 0.7 |
| Lipid components, mg/mL | | |
| Cholesterol | 15.0 ± 2.0 | 15.75 ± 2.6 |
| TG | 20.7 ± 3.5 | 20.7 ± 3.3 |
| S/D agents, ppm | | |
| TnBP | 738.3 ± 226.4 | 8.7 ± 3.5*** |
| TRITON ® X-45 | 2628 ± 75 | 8.8 ± 1.3*** |

*p < 0.05;
**p < 0.01;
***p < 0.001

4-SDS-PAGE

Figure 3:
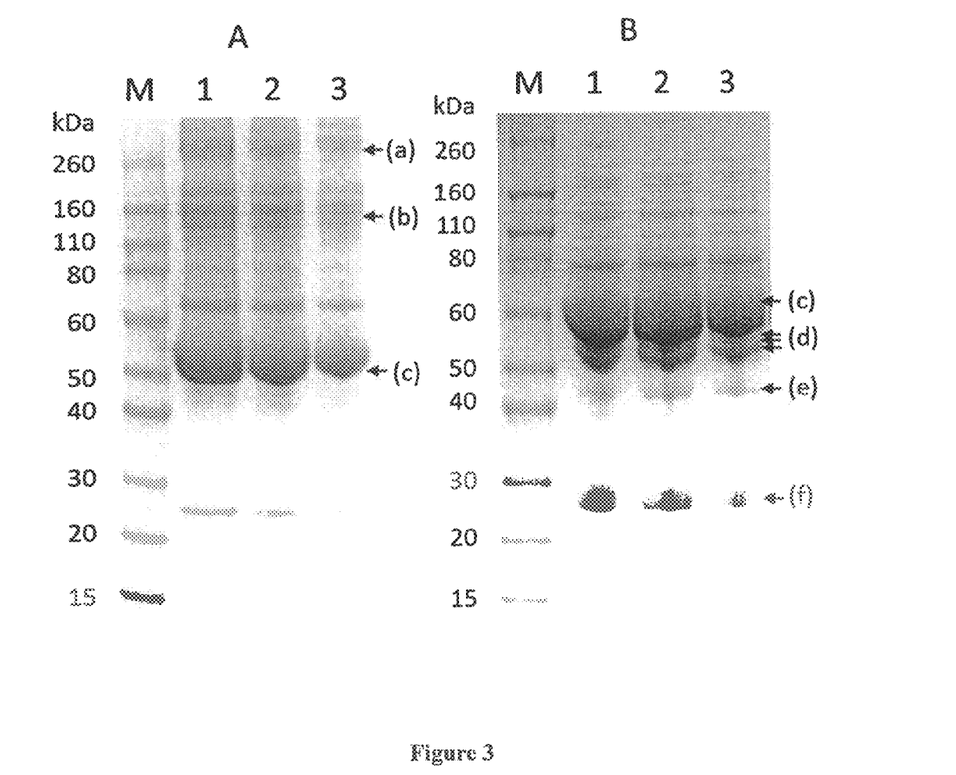
FIG. 3 shows the SDS-PAGE analysis of the platelet fractions under non-reduced (A) and reduced (B) conditions. Starting PC (lane 1), after solvent-detergent treatment and after one oil extraction (S/D-PC-O; 2), and after charcoal adsorption (S/D-PC-OC; 3). Novex sharp pre-stained protein marker (M). a: fibrinogen; b: IgG; c: albumin; d: fibrinogen subunits; e: IgG heavy chain; f: IgG light chain.

The SDS-PAGE analysis (FIG. 3) under non-reduced (A) and reduced (B) conditions did not reveal detectable change in the protein profile in the starting PC (1), S/D-PC-O (2), and S/D-PC-OC (3), evidencing major protein bands corresponding to the molecular mass of unreduced fibrinogen (a), unreduced IgG (b) and albumin (c).

5—Cell Cultures

Figure 4:
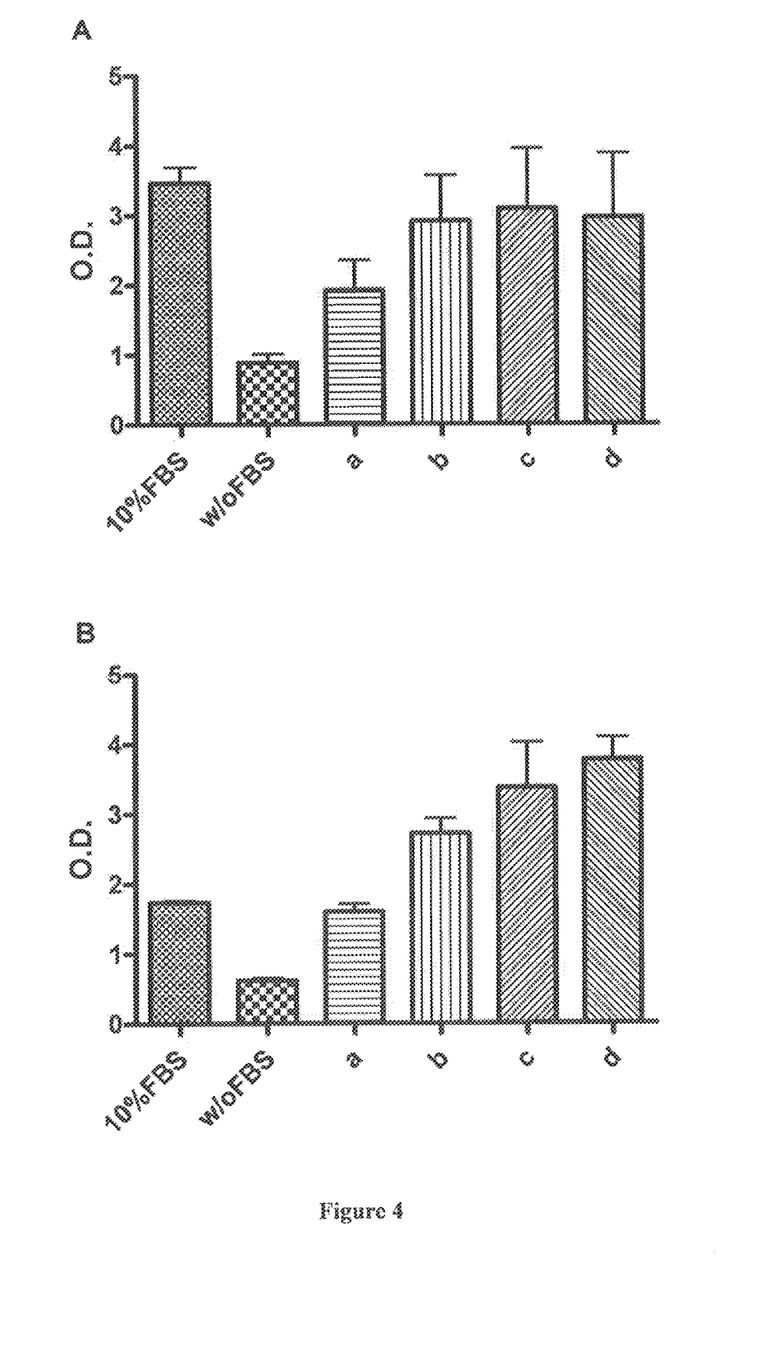
FIG. 4 depicts MTS cell proliferation data in MG63 (A) and SIRC (B) cell lines cultured in MEM supplemented with 10% (v/v) FBS (a); without FBS (b); and with 1 (c), 3 (d), 5 (e), and 10 (f) % of S/D-PC-OC. Cell viability was determined after 5 days of culture.

The results of the MTS assays (N=3) are shown in FIGS. 4A (MG63) and B (SIRC). Cell growth was high when the two cell lines were cultivated in the medium supplemented with 10% (v/v) FBS (a) but significantly reduced (p<0.05) in the control without FBS (b). Growth was also significantly higher (p<0.05) than in the control when the medium for both cell lines was supplemented with 1 to 10% of S/D-PC-OC. MTS values of MG63 cells in the presence of 1% S/D-PC-OC was less than that in the presence of 10% FBS but similar at concentrations between 3 and 10%. SIRC cell growth was not significantly different in the presence of 1% S/D-PC-OC and 10% FBS but significantly higher (p<0.05) when using increasing quantity of S/D-PC-OC from 3 to 10%. Cell morphology of both cell lines was normal when grown in the presence of 10% FBS or 1-10% S/D-PC-OC.

The invention claimed is:

1. A method for preparing a virally-inactivated growth factors-containing platelet lysate depleted of PDGF and VEGF comprising:
   a) containing a starting platelet concentrate with a solvent and a detergent;
   b) incubating for a period of at least 5 minutes to 6 hours, at a physiological pH or at a pH ranging from pH 6.8 to 8.2, and at a temperature within the range of from 2° C. to 50° C.;
   c) removing the solvent and detergent by oil extraction and obtaining an aqueous protein phase;
   d) mixing activated charcoal with the aqueous protein phase obtained in c);
   e) centrifuging the mixture of d) to pellet the charcoal; and f) recovering the supernatant from e), wherein the supernatant is virally-inactivated and depleted of PDGF and VEGF.

2. The method of claim 1 wherein the solvent is selected from the group consisting of di- or trialkylphosphates, di- or trialkylphosphates with different alkyl chains.

3. The method according to claim 2, wherein the solvent is the tri-n-butylphosphate (TnBP).

4. The method of claim 1 wherein the detergent is selected from the group consisting of polyoxyethylene derivatives of fatty acids, partial esters of sorbitol anhydrides, non-ionic detergents, sodium deoxycholate and sulfobetaines.

5. The method according to claim 4, wherein the detergent is oxyethylated alkylphenol or polysorbate 80.

6. The method of claim 1 wherein the concentration of both the solvent and detergent in step a) ranges from 0.2 to 5% in volume with respect to the volume of the starting platelet concentrate.

7. The method according to claim 1, wherein oil extraction is performed with a pharmaceutical grade oil, the oil being used in an amount of from 2 to 20 weight % based on the weight of the mixture of the platelet concentrate with the solvent and the detergent.

8. The method according to claim 7, wherein the oil is in the amount of from 5 to 15 weight %.

9. The method according to claim 8, wherein the oil is in the amount of from 5 to 10 weight %.

10. The method according to claim 1, wherein the activated charcoal is in an amount of from 50 to 250 g/l of said aqueous protein phase.

11. The method according to claim 1, further comprising centrifuging after step c) to pellet and remove any cell debris or insoluble material and recover the supernatant.

12. The method according to claim 1, wherein the starting platelet concentrate of step a) is prepared by at least one of apheresis and buffy-coat isolation from whole blood.

13. The method according to claim 1, wherein the starting platelet concentrate of step a) is obtained from pool platelet concentrates.

* * * * *